US012150787B2

(12) United States Patent
Zou et al.

(10) Patent No.: US 12,150,787 B2
(45) Date of Patent: Nov. 26, 2024

(54) CARDIAC MESH WITH PRESSURE SENSOR

(71) Applicant: IP2IPO INNOVATIONS LIMITED, London (GB)

(72) Inventors: Longfang Zou, London (GB); Mohammad Reza Bahmanyar, London (GB); Christopher Neil McLeod, Headington (GB)

(73) Assignee: IP2IPO INNOVATIONS LIMITED, London (GB)

( * ) Notice: Subject to any disclaimer, the term of this patent is extended or adjusted under 35 U.S.C. 154(b) by 1003 days.

(21) Appl. No.: 17/042,254

(22) PCT Filed: Feb. 27, 2019

(86) PCT No.: PCT/GB2019/050538
§ 371 (c)(1),
(2) Date: Sep. 28, 2020

(87) PCT Pub. No.: WO2019/186101
PCT Pub. Date: Oct. 3, 2019

(65) Prior Publication Data
US 2021/0045691 A1 Feb. 18, 2021

(30) Foreign Application Priority Data
Mar. 29, 2018 (GB) ...................................... 1805309

(51) Int. Cl.
A61B 5/00 (2006.01)
A61B 5/0215 (2006.01)
A61B 17/00 (2006.01)

(52) U.S. Cl.
CPC ............ *A61B 5/686* (2013.01); *A61B 5/0215* (2013.01); *A61B 5/6869* (2013.01);
(Continued)

(58) Field of Classification Search
CPC ..... A61B 5/686; A61B 5/0215; A61B 5/6869; A61B 17/0057; A61B 2017/00592; A61B 2017/00623; A61B 2562/0247
See application file for complete search history.

(56) References Cited

U.S. PATENT DOCUMENTS

| 5,212,988 A | 5/1993 | White |
| 2005/0065589 A1 | 3/2005 | Schneider et al. |

(Continued)

FOREIGN PATENT DOCUMENTS

| CN | 101620018 B | 10/2010 |
| EP | 1837638 A1 | 9/2007 |

(Continued)

OTHER PUBLICATIONS

International Search Report and Written Opinion for Patent Appl. No. PCT/GB2019/050474, dated May 10, 2019, 13 Pages.
(Continued)

*Primary Examiner* — Linda C Dvorak
*Assistant Examiner* — Abigail Bock
(74) *Attorney, Agent, or Firm* — Maine Cernota & Curran

(57) ABSTRACT

An implantable intracardiac apparatus for implantation in a wall of the heart to secure a pressure sensor thereto, the apparatus comprising: a mesh configured to collapse to enable it to be carried, by a catheter, to a deployment site in the heart, and to expand upon deployment from the catheter to provide a conformable mesh layer for securement against the wall of the heart; wherein the conformable mesh layer comprises an opening occupied by a compliant diaphragm that is flush with the mesh layer, or recessed with respect to the mesh layer, when the mesh layer is secured against the wall of the heart; the apparatus further comprising a can for holding said pressure sensor, and the compliant diaphragm provides a wall of the can.

17 Claims, 3 Drawing Sheets

(52) U.S. Cl.
CPC ...... *A61B 17/0057* (2013.01); *A61B 2017/00592* (2013.01); *A61B 2017/00597* (2013.01); *A61B 2017/00623* (2013.01); *A61B 2562/0247* (2013.01)

(56) References Cited

U.S. PATENT DOCUMENTS

| | | | |
|---|---|---|---|
| 2005/0288596 | A1 | 12/2005 | Eigler et al. |
| 2007/0032734 | A1* | 2/2007 | Najafi .............. A61B 5/0031 600/513 |
| 2007/0267708 | A1 | 11/2007 | Courcimault |
| 2010/0317977 | A1 | 12/2010 | Piaget |
| 2011/0036173 | A1 | 2/2011 | Chommeloux |
| 2012/0123284 | A1 | 5/2012 | Kheradvar |
| 2014/0275830 | A1 | 9/2014 | Osorio |
| 2016/0000344 | A1 | 1/2016 | Cao |
| 2019/0006577 | A1 | 1/2019 | Ghyselen |

FOREIGN PATENT DOCUMENTS

| | | | | |
|---|---|---|---|---|
| GB | 2552555 | A | | 1/2018 |
| GB | 2558708 | A | | 7/2018 |
| GB | 2558730 | A | | 7/2018 |
| JP | 20070256287 | A | | 10/2007 |
| WO | 20060056857 | A1 | | 6/2006 |
| WO | 20160028583 | A1 | | 2/2016 |
| WO | WO-2016028583 | A1 | * | 2/2016 ......... A61B 17/0057 |
| WO | 20160178196 | A2 | | 11/2016 |
| WO | 2018055367 | A2 | | 3/2018 |
| WO | 2018083486 | A1 | | 5/2018 |

OTHER PUBLICATIONS

International Search Report and Written Opinion for Patent Appl. No. PCT/GB2019/050538, dated May 23, 2019, 18 Pages.
Search Report for Great Britain Patent Appl. No. 1802824.1, dated Aug. 21, 2018, 4 Pages.
Office Action for U.S. Appl. No. 16/971,129 mail date Feb. 6, 2023, 26 pages.
Final Office Action for U.S. Appl. No. 16/971,129 mail date Jul. 12, 2023, 18 pages.
Office Action for U.S. Appl. No. 16/971,129 mail date Jan. 17, 2024, 19 pages.
Final Office Action for U.S. Appl. No. 16/971,129 mail date Jul. 1, 2024, 23 pages.

* cited by examiner

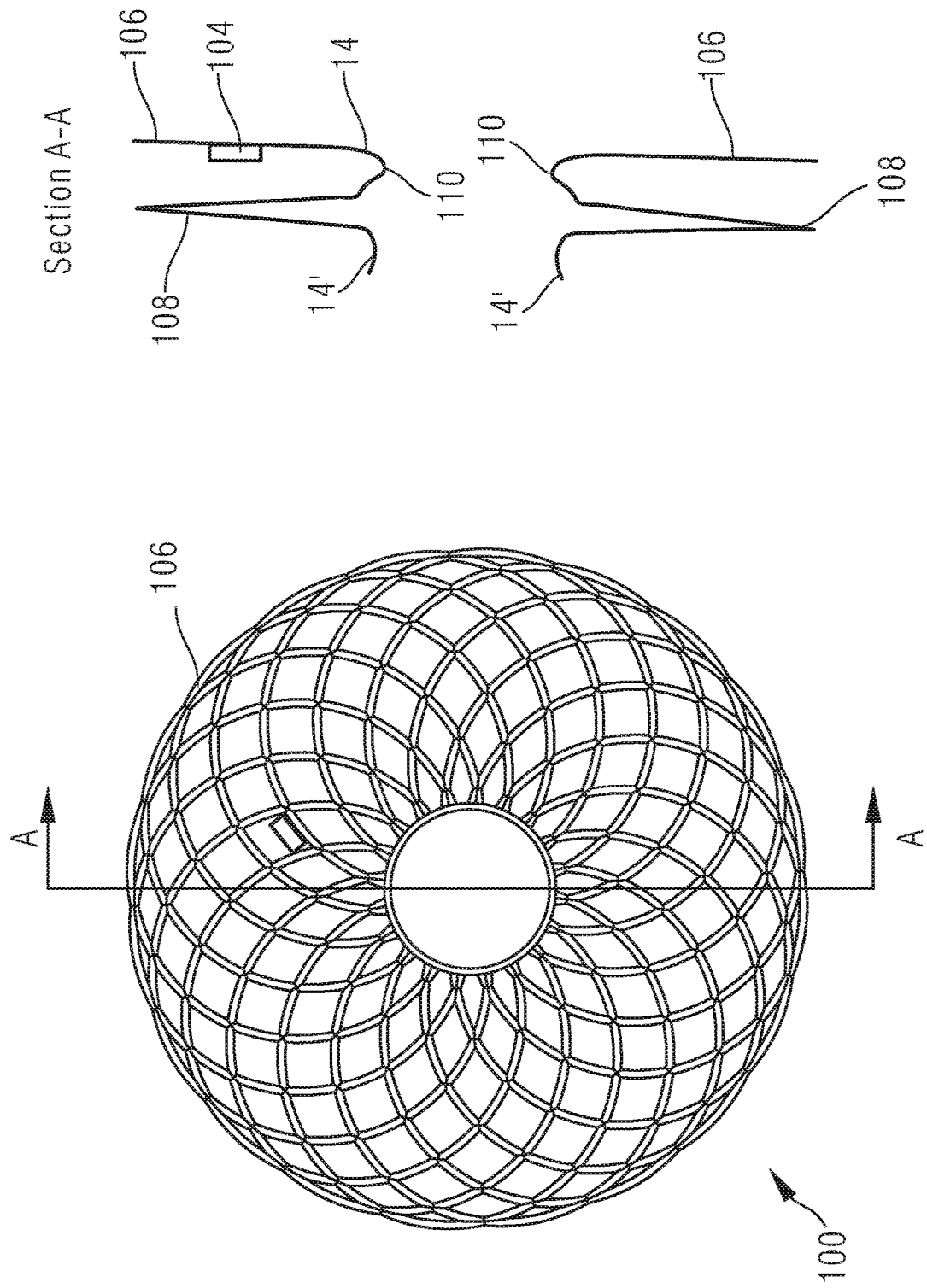

CARDIAC MESH WITH PRESSURE SENSOR

FIELD OF INVENTION

The present invention relates to methods and apparatus, and more particularly to intra-cardiac implants, and more particularly to devices for implantation in the interatrial septum, and still more particularly to pressure monitoring devices for implantation in the interatrial septum to monitor intra-cardiac pressure for example left atrial pressure.

BACKGROUND

Heart failure is defined clinically as a syndrome in which patients have symptoms and signs resulting from an abnormality of cardiac structure or function. Acute congestive heart failure (CHF) is the rapid onset of symptoms and signs of heart failure and may occur with or without previous cardiac disease. Indeed, heart disease is often stable in its initial stages but patient health may deteriorate rapidly, and may lead to recurrent hospitalization. Monitoring of intra-cardiac pressure may enable medical intervention before the development of clinical symptoms.

Catheters may be used to deploy monitoring devices into the heart. There are few implantable cardiac hemodynamic monitors on the market, some already in use while others have gone through clinical studies with successful safety records.

Atrial septal defects (ASD) may also be a problem. Such defects may allow oxygen-rich blood to leak into the oxygen-poor blood chambers in the heart. ASD is a defect in the septum between the heart's two upper chambers (atria). The septum is a wall that separates the heart's left and right sides.

Percutaneous device closure of an ASD involves the passage of a catheter into the heart through the femoral vein, often guided by fluoroscopy and echocardiography. An example of a percutaneous device, sometimes known as an occluder, has discs that can expand to a variety of diameters at the end of the catheter. The catheter is placed in the right femoral vein and guided into the right atrium. The catheter is guided through the atrial septal wall and one disc (left atrial) is opened and pulled into place against the septal wall. Once this occurs, the other disc (right atrial) is opened on the other side of the septal wall to hold the device in place in the septal wall.

A variety of systems have been proposed for intra-cardiac pressure monitoring. For example "*An Implantable Pressure Sensor for Long-term Wireless Monitoring of Cardiac Function—First Study in Man*" (Ahn et al., *J Cardiovasc Dis Diagn* 2016, 4:4) describes a wireless implantable hemodynamic monitor system known as Titan (RTM) (ISS Inc., MI, USA). This system comprises two parts; an implantable, telemetric sensor (no implanted power source/battery is required) and an extracorporeal companion readout electronics and user interface. There is no physical connection between the implant and the rest of the system (extracorporeal components). Using radio frequency (RF) magnetic telemetry, the receiver transmits power to the sensing implant and communicates with it. The RF interface requires very little power. The wireless communication transmits detailed cardiac pressure waveforms and implant information such as implant power enabling advanced dynamic power transmission. The miniature implant has two main components; polyether ketone housing and a cylindrical pressure-sensing probe placed inside it. The probe contains a miniature micro-electromechanical pressure sensor along with custom electronics and a telemetry antenna.

US20120123284 describes a wireless hemodynamic monitoring system that is implantable or integratable within or on an implantable cardiac device such as a heart valve, an annuloplasty ring, a mitral valve sewing ring, or the like. This monitoring system aims to provide real-time sensing of hemodynamic parameters, non-limiting examples of which include hydrostatic pressure, blood oxygen/carbon dioxide partial pressures, blood velocity (i.e., blood flow rate), blood viscosity, blood biochemistry, etc., depending on the need of the patient.

SUMMARY

Aspects and embodiments of the present disclosure are set out in the appended claims.

In an aspect there is provided an apparatus for implantation in a wall of the heart to secure a pressure sensor thereto. Examples of such apparatus include occluder devices, which may be configured for deployment into atrial septal defects (ASD).

The apparatus comprises a mesh configured to collapse to enable it to be carried, by a catheter, to a deployment site in the heart, and to expand upon deployment from the catheter to provide a deformable mesh layer which is operable to conform to a surface of the wall of the heart. When held closely against the surface of the wall of the heart, this mesh layer can conform to it sufficiently closely to enable endothelialisation of the mesh. This conformable mesh layer comprises an opening occupied by a compliant diaphragm that, when the mesh layer is secured against the wall of the heart in this way, is flush with the mesh layer, or recessed with respect to it. That is to say, the diaphragm does not protrude beyond the mesh, and the diaphragm and the mesh layer may occupy substantially the same plane—e.g. both may closely conform to the ordinary surface of the wall of the heart into which they are implanted.

In this aspect, the apparatus further comprises a can for holding said pressure sensor, and the compliant diaphragm provides a wall of that can. Generally the compliant diaphragm encloses, in the can, an internal volume which encapsulates the pressure sensor. It may also be filled with a biocompatible liquid which surrounds the pressure sensor. The compliant diaphragm, and any liquid contents of that internal volume can therefore together mediate pressure from the external surface of the compliant diaphragm to the sensor.

The can may be arranged so that when the conformable mesh layer is secured to the wall of the heart the can is held between the wall of the heart and the diaphragm. This may comprise the can being held in a recess in the wall of the heart, such as a defect. The defect may be native or surgically created. In some embodiments, the defect need not be present and the can may simply be seated against the wall of the heart.

Where a can and diaphragm are present, the mesh layer provides a flange around the opening of the can. This flange may occupy a region of the surface of the wall of the heart which completely surrounds the opening. For example, the flange may be an annular disc shape with the opening at its centre.

The mesh may be made by any appropriate method. For example it may be woven or knitted, or formed by moulding a resilient material. However it is manufactured the largest dimension (whether width or length) of the spacing between adjacent wires in the mesh may be selected to enable endothelialisation of the layer into the wall of the heart. This spacing between adjacent wires may be referred to as the aperture size of the mesh. Typically, the size of the diaphragm covered opening is larger than the aperture size and also large enough to inhibit endothelialisation of the diaphragm. The opening may be round, for example its boundary may be circular or oval. Such a boundary may have a minimum radius of curvature selected to inhibit endothelialisation of the diaphragm.

Prior to deployment, the can may be filled with a biocompatible liquid such as isotonic saline.

The diaphragm may comprise a permeable membrane, such as a fabric of interwoven fibres. This may enable liquid in the can to be replaced with blood after the can is deployed into the heart. The permeable membrane may thus allow formation of thrombus in the capsule, but contain the thrombus therein.

In an aspect there is provided an interatrial shunt device comprising a mesh configured to collapse to enable it to be carried, by a catheter, to a deployment site in the heart. The deployment site may comprise a native or surgically created defect in a septum, such as the inter-atrial septum. The mesh is configured to expand upon deployment from the catheter to provide two broad, flat, mesh flanges joined together by a narrower waist. Each of the flanges comprise an opening, wherein a boundary of the opening in the first flange is joined to the boundary of the opening in the second flange by an intermediate portion, which may also comprise mesh, to form the waist between the two flanges. This intermediate portion may be adapted to hold open the defect in the septum to allow a shunt of fluid pressure through the septum. For example it may comprise a barrel construction.

The mesh flanges, as with the other embodiments described herein may comprise a deformable mesh which is operable to conform to a surface of the wall of the heart. When held closely against the surface of the wall of the heart, this mesh layer can conform to it sufficiently closely to enable endothelialisation of the mesh.

Such embodiments may comprise a can closed by a diaphragm as claimed and described elsewhere herein (e.g. with reference to FIG. 1, below). In these embodiments, the can may be adapted to lie between the mesh flange and the wall rather than being disposed in the defect. In these embodiments one of the conformable mesh flanges may comprise two openings. A first opening covered by the diaphragm which closes the can, and a second opening, connected via the intermediate portion, to the other mesh flange for holding open the shunt/defect to provide a flow path through the interatrial septum.

In such embodiments the can and diaphragm need not be used at all, and the sensor may be carried directly on the mesh or integrated with the mesh. For example, the sensor may be clamped onto a wire of the mesh, and the antenna may be provided by a wire of the mesh or interwoven with the mesh.

Although most of the apparatus described herein uses mesh as a carrier to hold the apparatus in position in the heart, in some embodiments a carrier other than mesh may be used. For example, in an aspect there is provided an implantable device for sensing pressure in the left atrium, the device comprising: a carrier for insertion through a hole in the septal wall between the left atrium and the right atrium; wherein the carrier is compressible from an operational configuration to a compressed configuration for delivery via a catheter; wherein in the operational configuration the carrier comprises a first flange and a second flange coupled via an intermediate portion, wherein the first flange and the second flange have an larger diameter than the intermediate portion, and are configured so that an inner edge of each flange sits either side of the septal wall and carries the intermediate portion in the hole in the septal wall, and wherein the intermediate portion carries a pressure sensor such that the pressure sensor does not extend beyond an inner edge of one of the flanges.

The pressure sensor may be disposed in a can secured to the intermediate portion of such an apparatus. The can may have an opening that, when the apparatus is secured to the septal wall, is presented to the left atrium and is covered by a compliant diaphragm.

In an embodiment the size of the opening is large enough to inhibit endothelialisation of the diaphragm.

The boundary of the opening may be round, for example it may be circular or oval.

Further embodiments are envisaged. It is to be understood that any feature described in relation to any one embodiment may be used alone, or in combination with other features described, and may also be used in combination with one or more features of any other of the embodiments, or any combination of any other of the embodiments.

BRIEF DESCRIPTION OF DRAWINGS

Embodiments of the disclosure will now be described in detail with reference to the accompanying drawings, in which:

FIG. 1 shows three views of an implantable intracardiac pressure sensing apparatus, including:

FIG. 3 shows a further implantable apparatus which can be used to install a pressure sensor in a wall of the heart.

In the drawings like reference numerals are used to indicate like elements.

SPECIFIC DESCRIPTION

Figure 1A:
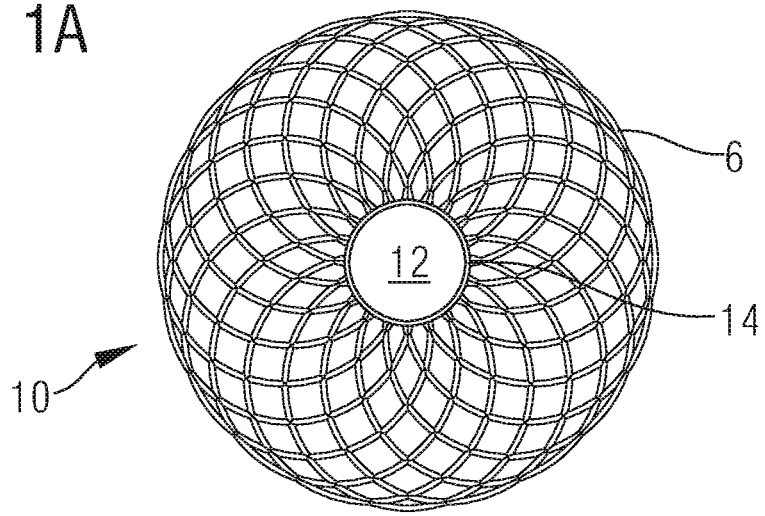
FIG. 1A which shows a view of the distal end of the apparatus.
Figure 1B:
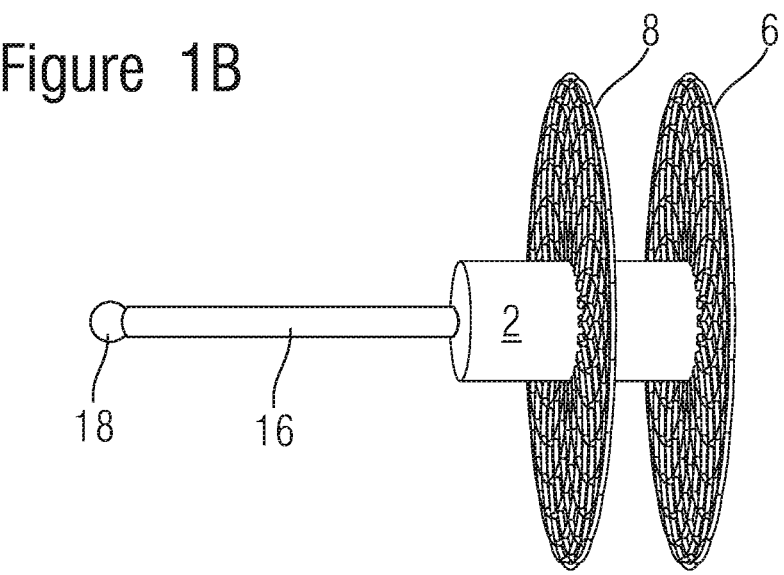
FIG. 1B which shows a perspective view of the side of the apparatus.
Figure 1C:
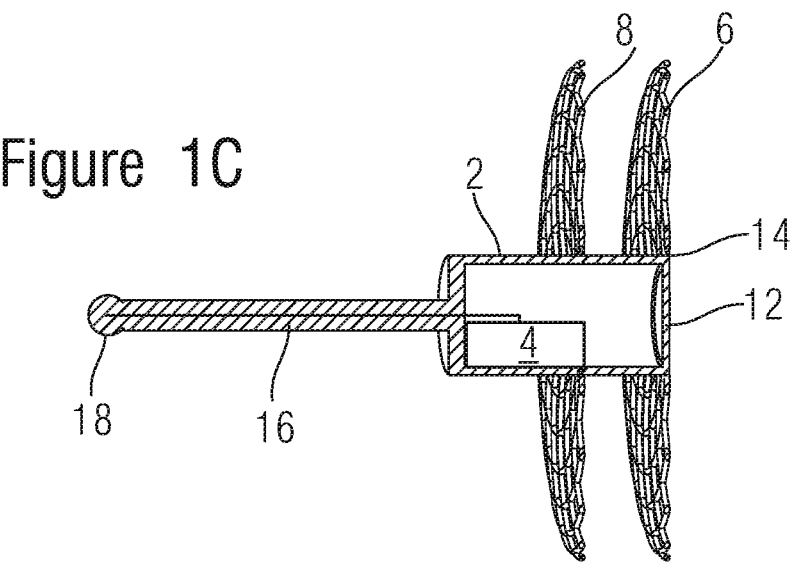
FIG. 1C which shows a cutaway view of the side of the apparatus seen in FIG. 1B.

FIG. 1 shows an implantable intracardiac apparatus 10 for implantation in a wall of the heart.

The apparatus 10 comprises a rigid can 2 for encapsulating a sensor 4. The can 2 may be cylindrical, and may be closed at one end. An antenna 16 is secured to the closed end of the can and electrically connected to the sensor 4 for providing RF electrical signals to/from the sensor 4. The free end of the antenna 16 comprises an atraumatic tip 18.

The other end of the can 2 may be open but covered by a compliant diaphragm 12. The can 2 comprises an internal volume, enclosed by the compliant diaphragm 12 in which the sensor can be held. The volume around the sensor 4 in the can may be filled with a biocompatible fluid, such as isotonic saline.

The apparatus 10 also comprises two collapsible flanges 6, 8 which surround the can 2, spaced apart from each other along its length and protruding radially outward from it. When expanded, as shown in FIG. 1, the flanges 6, 8 provide substantially annular discs around the can 2. In this expanded formation, the flanges 6, 8 may be flat, but they are made from a deformable material so that they can conform to a surface of a structure into which the the can 2 is implanted.

Each flange 6, 8 may comprise a biocompatible mesh, which may be provided by a wire knitted or woven to provide the mesh. The wire may be resilient so that it will self-expand upon deployment from a catheter. It may comprise a memory metal such as a nickel-titanium alloy, e.g. nitinol. As illustrated in FIG. 1A, the weave pattern of the mesh may be any appropriate textile weave or knit, but other weave patterns may be used. Whatever knit or weave pattern is used, the mesh which makes up the flanges 6, 8 may be arranged so that the openings between the wires in the expanded state are of the correct size to promote endothelialisation of the mesh when it is deployed against a surface of a wall of the heart. The size of the opening 14 at the end of the can 2 (e.g. the opening covered by the membrane 12) is generally greater than this size and is typically large enough to inhibit or prevent endothelialisation of the diaphragm.

The first mesh flange 6 is secured to the distal end of the can 2, e.g. the outer surface of the can at or near its distal end. The radially inward edge of the flange 6 may circumscribe the opening 14, and may be secured to the outer wall of the can 2 around its circumference. Thus when expanded, the first mesh flange 6 may spread out around the diaphragm 12 which covers (and closes) the open distal end of the can 2.

The second mesh flange 8 is spaced from the first mesh flange 6 proximally along the surface of the can 2. This second mesh flange 8 may also be arranged around a circumference of the radially outer surface of the can 2. Although illustrated as a single layer, either or both of the two mesh flanges 6, 8 may comprise two or more layers of mesh as illustrated in FIG. 2.

The antenna, which may comprise a so-called "whip" antenna, protrudes from the proximal end of the can and may be aligned with the centre of the can (e.g. it may be aligned with a central axis of a cylindrical can). The antenna may comprise an atraumatic tip at its proximal end.

A sensor 4 disposed inside the can is electrically connected to the antenna 16 for sending and receiving electromagnetic signals (e.g. RF signals). This sensor 4 may comprise a passive device, adapted to resonate in response to a received signal such that the resonant response can be transmitted back, via the antenna, to a detector outside the body of the patient. Examples of such passive devices comprise piezoelectric acoustic wave devices such as surface acoustic wave (SAW) and bulk acoustic wave (BAW) based pressure sensors. One example of such a pressure sensor is described in PCT/GB2017/052802 the entire disclosure of which is incorporated herein by reference. Another example of such a sensor is described in PCT/GB2017/053313 the entire disclosure of which is incorporated herein by reference. Other types of sensors may be used. As illustrated in FIG. 2C, the sensor 4 may also be electrically connected to the second mesh flange 8, in series between the antenna 16 and the second mesh flange 8, so that the second mesh flange 8 can act as a ground plane for the antenna. Any part of the mesh structure may be used to provide a ground plane in this way.

The mesh flanges 6, 8 are operable to collapse radially inward (toward the can 2) to reduce the radial extent of the apparatus. For example, the first flange may be arranged so that, as its radially outer edge is displaced distally, the first flange 6 contracts radially to provide a distal facing trumpet shape with the can at its proximal end. Likewise, the second flange 8 may be arranged so that, as its radially outer edge is displaced proximally, it contracts radially to provide a proximal facing trumpet shape which surrounds the proximal end portion of the can, and which may also surround all or part of the antenna. This can allow the device to be held inside a catheter, generally at or near the distal end of the catheter. A catheter can thus provide a sheath around the apparatus which restrains the flange in a collapsed state until it is deployed.

The diaphragm is generally arranged at the distal end of the can, and generally comprises a compliant material which is operable to allow the diffusion of fluids through it, but to inhibit or prevent bulk flow.

Generally, when the apparatus is first deployed into a patient, the volume inside the can 2, enclosed by the diaphragm 12, is filled with a biocompatible liquid such as isotonic saline. This liquid surrounds the sensor 4 in the can. The diaphragm may be configured so that, after deployment the biocompatible liquid may diffuse out of the can to be displaced by a biological liquid such as blood, which may later form thrombus around the sensor. FIG. 2 illustrates a method of deploying an apparatus 10 such as that illustrated in FIG. 1 into a defect 24 in a wall 22 of the heart. For example the defect 24 may be a hole through the interatrial septum 22, and it may be a native, pre-existing, defect. It may however also be surgically created for the purpose of deploying the apparatus 10 of the present disclosure.

FIG. 2 comprises a series of illustrations to show a sequence of operations involved in deploying the apparatus.

Figure 2A:
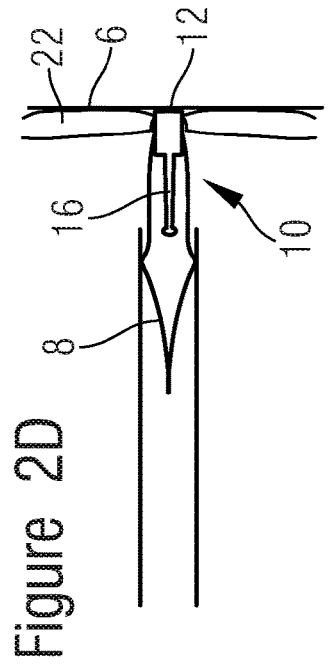
FIG. 2 illustrates a method of deploying a pressure sensing apparatus such as that illustrated in FIG. 1.

FIG. 2A illustrates a catheter 20 carrying, in a collapsed state, an implantable intracardiac apparatus 10 for implantation in a defect in a wall of the heart 22.

Figure 2B:
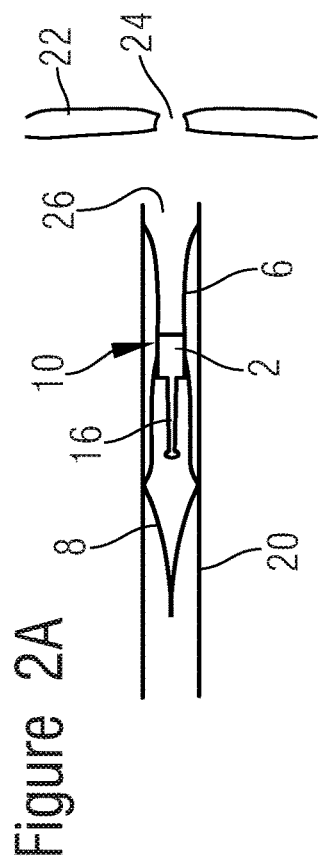
Figure 2C:
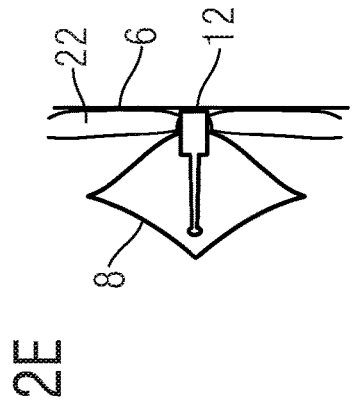

FIG. 2B and FIG. 2C illustrates the catheter 20 and implantable apparatus 10 in situ in the defect 24 in a partially deployed state.

Figure 2D:
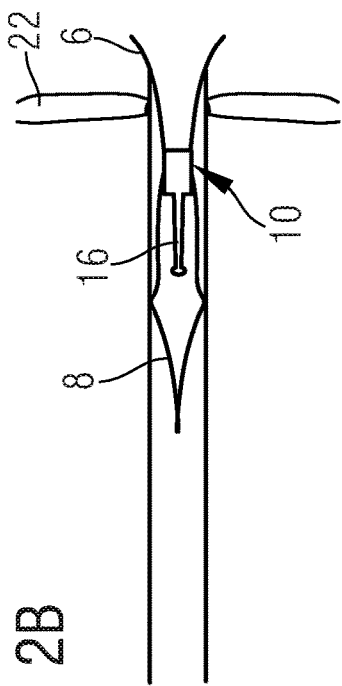

FIG. 2D illustrates the apparatus 10 in situ with the first flange 6 fully deployed and conformed to a surface of the wall 22 of the heart around the defect 24.

Figure 2E:
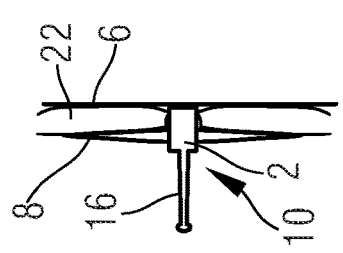
Figure 2F:
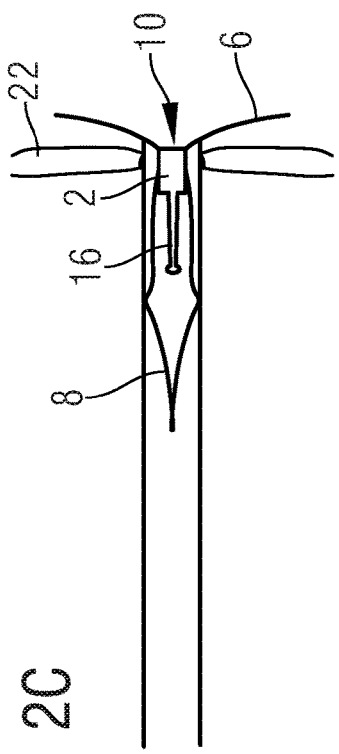

FIG. 2E illustrates the arrangement in FIG. 2D as the second mesh flange 8 is being deployed. FIG. 2F illustrates the apparatus 10 when fully deployed in the defect 24.

FIG. 2A shows a diagram of a section through the distal end of a catheter 20. The catheter 20 is sized for deployment into the chambers of the heart via an atrial or venous catheterisation process. For example it may be sized for deployment via an atrial or venous catheterisation process into the heart of an adult human subject. The distal end of the catheter 20 has an opening 26 for deployment of the apparatus 10.

An apparatus 10 such as that described above with reference to FIG. 1 is disposed at the distal end of the catheter near to the opening in the catheter. The first flange 6 of the apparatus 10 is restrained in a collapsed state by the catheter 20 so that it extends distally forwards in front of the can 2 in a trumpet shape having the can 2 at its proximal end. The second flange 8 is also restrained in a collapsed state by the catheter 20, but it is bent back proximally behind the can 2, with the can 2 at its distal end. In this collapsed state, the second mesh flange 8 surrounds the antenna 16 of the apparatus.

As illustrated in FIG. 2A, the second mesh flange 8 may comprise two parts. In its collapsed state, the first part extends proximally back from the can and radially outward toward the wall of the catheter 20. A second part is joined to the proximal end of the first part by a bend in the mesh. The second part tapers radially inward towards its proximal end.

To deploy the apparatus 10 the distal end of the catheter 20 is advanced to a first chamber of the heart (typically the right atrium) on a first side of the septal defect 24. As illustrated in FIG. 2B, the distal end of the catheter is then advanced through the defect 24 to second chamber of the heart (typically the left atrium) on the second side of the septal defect 24.

An outer part of the catheter 20 can then be retracted relative to the apparatus 10 (e.g. a sheath of the catheter 20 is pulled back whilst holding the apparatus 10 in position to begin to release the apparatus). It can be seen in this drawing that the septal defect 24 may be occluded, at least in part, by the can.

As illustrated in FIG. 2B and FIG. 2C, as the restraint provided by the catheter 20 is removed, the first mesh flange 6 begins to expand in the second chamber of the heart on the second side of the septal defect 24. Once the first mesh flange 6 is fully deployed, as illustrated in FIG. 2D, it forms a layer of mesh against a region of the surface of the septum 22 which surrounds the defect 24. This layer conforms closely to the surface of the septum 22. At the middle of this region, surrounded by the mesh flange, is the diaphragm 12 at the distal end of the can 2. The mesh flange 6 and the diaphragm 12 are flush with each other—e.g. they present a substantially continuous surface which does not protrude into the left atrium beyond the thickness of the layer of mesh. It will thus be appreciated that the diaphragm 12 is exposed to intracardiac pressure in the left atrium but provides a very low profile in the left atrium. The diaphragm 12 may mediate pressure to the sensor 4 contained in the can 2.

As shown in FIG. 2E, once the first mesh flange 6 is fully deployed against the septal wall 22 of the second chamber of the heart the second mesh flange 8 is deployed. This is done by releasing the second flange from the catheter and advancing it distally and radially outward until it lies against, and conforms to the septal wall 22 on the first side of the septal defect 24.

It will be appreciated in the context of the present disclosure that the can need not be disposed in a defect in the wall of the heart and instead the defect may remain open. For example, the can may be sufficiently small t be held between one of the two mesh flanges and the wall of the heart. In these and other embodiments the two mesh flanges may be joined by an intermediate portion of mesh in the form of a tube (e.g. like a waist in an hourglass). This intermediate portion can hold the defect open. This may be used to create an interatrial shunt. In these and other embodiments the sensor may be secured to the mesh flange. For example it may be disposed between the flange and the wall of the heart. In these cases, a very low profile can may be used, or the can and diaphragm may be absent—the sensor apparatus may be deployed directly in the chamber of the heart with the antenna secured to the mesh.

FIG. 3 shows one example of such an interatrial shunt device 100 for implantation in the septum. FIG. 3 shows an end view of the apparatus 100, when expanded and shows a cross-section A-A at the line A-A indicated in the end-view.

This interatrial shunt device 100 comprises a mesh, having the features of the mesh described above with reference to FIG. 1. This mesh is arranged to provide a first flange 106 and a second flange 108. A pressure sensor 104, such as any pressure sensor described herein, is secured to the mesh of the first flange 6. For example, the pressure sensor 104 may be clamped to the wire which makes up the mesh. This may be done by providing a channel or trench through a first part of the sensor device 104, and securing a second part of the sensor device to the first part with the wire held between the two parts. Other methods of clamping may be used—for example the sensor 104 may be housed in a ceramic body which is moulded for clamping to the mesh. The sensor may be beneath the mesh—e.g. it may be arranged so that, when the interatrial shunt is secured to the wall of the heart, the sensor is held between the mesh and the wall of the heart.

The second flange 108 and the first flange 106 each surround an opening 14. The opening 14 in the first flange is joined to the opening 14' in the second flange by an intermediate portion 110 of mesh. This intermediate portion 110 is substantially cylindrical, e.g. barrel shaped, and provides a mesh wall around the opening 14 which links the two flanges 106, 108. In use, this interatrial shunt apparatus 100 is deployed into a defect in the septum exactly as described above with reference to FIG. 2, but of course instead of occluding the defect, the intermediate portion 110 holds the defect open to provide a flow path for blood to equalize pressure between the two chambers of the heart.

The mesh flanges 106, 108, as with the flanges (6, 8; FIG. 1) of the other embodiments described herein may comprise a deformable mesh which is operable to conform to a surface of the wall of the heart. When held closely against the surface of the wall of the heart, this mesh layer can conform to it sufficiently closely to enable endothelialisation of the mesh.

A variety of sensors may be used with the embodiments of the present disclosure. As described above, these sensors may comprise passive sensors such as SAW or BAW sensors. One such a SAW based sensor comprises: a first transducer arranged to provide a pressure dependent signal in response to alternating electrical signals of a first frequency band; a second transducer arranged to provide a reference signal in response to alternating electrical signals of a second frequency band different from the first frequency band; and an antenna coupling for connection to the antenna at the proximal end of the can. The sensor can thus receive and respond to said signals via the antenna. The antenna coupling may be coupled to the first transducer and to the second transducer for coupling both transducers to the antenna. The pressure dependence of the response signal provided by the first transducer is associated with a pressure dependent change in a resonance characteristic of the first transducer. In these embodiments the second transducer may be arranged so that pressure dependent changes in the resonance characteristic of the second transducer are less than those of the first transducer. The first transducer and the second transducer may be connected to the antenna in parallel with each other. The antenna may be adapted for sending and receiving radio frequency (RF) signals, and may have a bandwidth which encompasses the first frequency band and second frequency band. In these and other types of sensor, the pressure dependence of the response provided by the first transducer may be associated with deflection of a deflectable member by changes in intravascular pressure; and the reference response is associated with a reference member arranged to be deflected less than the deflectable member by those same changes in intravascular pressure. One such sensor is described in detail in PCT/GB2017/052802, the entire disclosure of which is incorporated herein by reference.

In an embodiment the sensor comprises a bulk acoustic wave (BAW) resonator arranged to be deflected by changes in fluid pressure to provide a pressure dependent sensing signal; and an acoustic reflector arranged to separate the BAW resonator from the fluid and to mediate pressure from the intravascular fluid to the BAW resonator; wherein the acoustic reflector comprises a layer structure arranged to provide a series of transitions in acoustic impedance between the intravascular fluid and the BAW resonator. The layer structure may comprise a flexible layer which encloses an additional fluid layer, separate from the fluid whose pressure is to be sensed, between the flexible layer and the BAW resonator. This additional fluid layer may comprise a gas layer. The additional fluid layer may be held in a sealed enclosure provided at least in part by the flexible layer. In an embodiment the body of this sensor comprises a cavity of fluid at a reference pressure arranged so that the BAW resonator can be deflected into the cavity in response to changes in pressure of the fluid outside the sensor. One such sensor is described in detail in PCT/GB2017/053313, the entire disclosure of which is incorporated herein by reference. Any appropriate sensor may be use, but there are certain advantages to the passive sensor designs described herein.

To the extent that certain methods described herein may be applied to the living human or animal body, it will be appreciated that such methods may not provide any therapeutic effect. In addition, it will be appreciated that such methods may be applied ex vivo, to tissue samples that are not part of the living human or animal body. For example, the methods described herein may be practiced on meat, tissue samples, cadavers, and other non-living objects. For example, they may be used for monitoring interatrial pressure during surgical training carried out by medical professionals in training.

Any feature of any one of the examples disclosed herein may be combined with any selected features of any of the other examples described herein. For example, features of methods may be implemented in suitably configured hardware, and the configuration of the specific hardware described herein may be employed in methods implemented using other hardware.

It will be appreciated from the discussion above that the embodiments shown in the Figures are merely exemplary, and include features which may be generalised, removed or replaced as described herein and as set out in the claims. With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention.

The invention claimed is:

1. An implantable intracardiac apparatus for implantation in a wall of the heart to secure a pressure sensor thereto, the apparatus comprising:
   a mesh configured to:
   collapse to enable it to be carried, by a catheter, to a deployment site in the heart, and to
   expand upon deployment from the catheter to provide a conformable mesh layer for securement against the wall of the heart;
   wherein the conformable mesh layer comprises an opening occupied by a compliant diaphragm that is flush with the mesh layer, or recessed with respect to the mesh layer, when the mesh layer is secured against the wall of the heart;
   the apparatus further comprising a can for holding said pressure sensor, and the compliant diaphragm provides a wall of the can,
   wherein the diaphragm comprises a permeable membrane.

2. The apparatus of claim 1 wherein the can is arranged so that when the conformable mesh layer is secured to the wall of the heart the can is held between the wall of the heart and the diaphragm.

3. The apparatus of claim 2 wherein the can is for implantation in the wall of the heart, and the mesh layer provides a flange around the opening.

4. The apparatus of claim 3 wherein the mesh layer is arranged so that upon implantation of the can into a surface of the wall of the heart, the flange lies flush against a region of the surface surrounding the opening.

5. The apparatus of claim 1 wherein the conformable mesh layer has a mesh aperture size selected to enable endothelialisation of the layer into the wall of the heart and wherein the size of the opening is greater than the mesh aperture size.

6. The apparatus of claim 1 further comprising the pressure sensor.

7. The apparatus of claim 6 wherein the pressure sensor comprises a passive device.

8. The apparatus of claim 1 wherein the boundary of the opening has a minimum radius of curvature of at least 2 mm.

9. The apparatus of claim 1 wherein the can is filled with a biocompatible fluid.

10. The apparatus of claim 1 wherein the permeable membrane is configured to allow formation of thrombus in the capsule, and to contain the thrombus therein.

11. The apparatus of claim 1 wherein the can encapsulates a sensor for sensing of intracardiac pressure when the apparatus is secured to the wall of the heart.

12. An occluder device for closing a defect in the interatrial septum, wherein the device comprises an apparatus for implantation in a wall of the heart to secure a pressure sensor thereto, the apparatus comprising:
   a mesh configured to:
   collapse to enable it to be carried, by a catheter, to a deployment site in the heart, and to
   expand upon deployment from the catheter to provide a conformable mesh layer for securement against the wall of the heart;
   wherein the conformable mesh layer comprises an opening occupied by a compliant diaphragm that is flush with the mesh layer, or recessed with respect to the mesh layer, when the mesh layer is secured against the wall of the heart;
   the apparatus further comprising a can for holding said pressure sensor, and the compliant diaphragm provides a wall of the can,
   wherein the diaphragm comprises a permeable membrane.

13. An interatrial shunt device comprising an apparatus for implantation in a wall of the heart to secure a pressure sensor thereto, the apparatus comprising:
a mesh configured to:
collapse to enable it to be carried, by a catheter, to a deployment site in the heart, and to
expand upon deployment from the catheter to provide a conformable mesh layer for securement against the wall of the heart;
wherein the conformable mesh layer comprises an opening occupied by a compliant diaphragm that is flush with the mesh layer, or recessed with respect to the mesh layer, when the mesh layer is secured against the wall of the heart;
the apparatus further comprising a can for holding said pressure sensor, and the compliant diaphragm provides a wall of the can, wherein the conformable mesh layer further comprises a second opening, and mesh elements adapted to hold open a flow path through the interatrial septum,
wherein the compliant diaphragm comprises a permeable membrane.

14. The interatrial shunt of claim 13 wherein the mesh elements are arranged to provide a barrel construction.

15. The apparatus of claim 1 wherein the mesh is self-expanding upon deployment from the catheter.

16. The apparatus of claim 1 wherein the permeable membrane comprises a fabric of interwoven fibres.

17. The apparatus of claim 1 wherein the biocompatible fluid comprises isotonic saline.

* * * * *